US011089278B2

(12) United States Patent
Themelis

(10) Patent No.: US 11,089,278 B2
(45) Date of Patent: Aug. 10, 2021

(54) IMAGE-PROCESSING DEVICE, FLUORESCENCE OBSERVATION DEVICE AND METHOD FOR EMULATING A FIRST TYPE OF FLUORESCENCE OBSERVATION DEVICE ON A SECOND TYPE OF FLUORESCENCE OBSERVATION DEVICE

(71) Applicant: Leica Instruments (Singapore) Pte. Ltd., Singapore (SG)

(72) Inventor: George Themelis, Lindau (DE)

(73) Assignee: Leica Instruments (Singapore) Pte. Ltd., Singapore (SG)

( * ) Notice: Subject to any disclaimer, the term of this patent is extended or adjusted under 35 U.S.C. 154(b) by 0 days.

(21) Appl. No.: 16/716,592

(22) Filed: Dec. 17, 2019

(65) Prior Publication Data

US 2020/0204776 A1 Jun. 25, 2020

(30) Foreign Application Priority Data

Dec. 21, 2018 (EP) .................................. 18215010

(51) Int. Cl.
| | | |
|---|---|---|
| *A61B 1/04* | (2006.01) | |
| *H04N 9/76* | (2006.01) | |
| *G02B 21/00* | (2006.01) | |
| *G02B 21/16* | (2006.01) | |
| *G02B 21/36* | (2006.01) | |

(52) U.S. Cl.
CPC .............. *H04N 9/76* (2013.01); *A61B 1/043* (2013.01); *G02B 21/0012* (2013.01); *G02B 21/16* (2013.01); *G02B 21/365* (2013.01)

(58) Field of Classification Search
CPC ...... H04N 9/76; A61B 1/043; G02B 21/0012; G02B 21/16; G02B 21/365
See application file for complete search history.

(56) References Cited

U.S. PATENT DOCUMENTS

| | | |
|---|---|---|
| 6,969,843 B1 | 11/2005 | Beach et al. |
| 2014/0378843 A1 | 12/2014 | Valdes et al. |

(Continued)

FOREIGN PATENT DOCUMENTS

| | | |
|---|---|---|
| JP | 2003159210 A | 6/2003 |
| JP | 2004000505 A | 1/2004 |

*Primary Examiner* — John R Schnurr
(74) *Attorney, Agent, or Firm* — Hodgson Russ LLP

(57) ABSTRACT

An image-processing device (64) for a fluorescence observation device (1), such as a microscope or endoscope, emulates a first type (82) of fluorescence display device on a second type (63) of fluorescence display device (1). Proficient use of a fluorescence observation device (1) for surgery requires years of training and experience. As technology quickly advances, new types of fluorescence observation devices provide different and more information than older types of fluorescence observation devices, however adoption of newer types is slow because new training is needed. The present disclosure facilitates the switch from one type of fluorescence observation device to another by providing a type-emulation module (108), which allows the imaging result obtained from the first type of fluorescence observation device to be emulated on the second type. The type-emulation module (108) is applied to a digital fluorescence image (20) in which the fluorescence of a fluorescing fluorophore (8) is recorded.

13 Claims, 3 Drawing Sheets

(56) References Cited

U.S. PATENT DOCUMENTS

| | | |
|---|---|---|
| 2015/0208958 A1 | 7/2015 | Kaku |
| 2017/0237958 A1 | 8/2017 | Themelis |
| 2017/0280029 A1* | 9/2017 | Steiner ................. A61B 1/0005 |
| 2018/0299382 A1 | 10/2018 | Yamada et al. |
| 2019/0117078 A1* | 4/2019 | Sharma ................. A61B 5/015 |

* cited by examiner

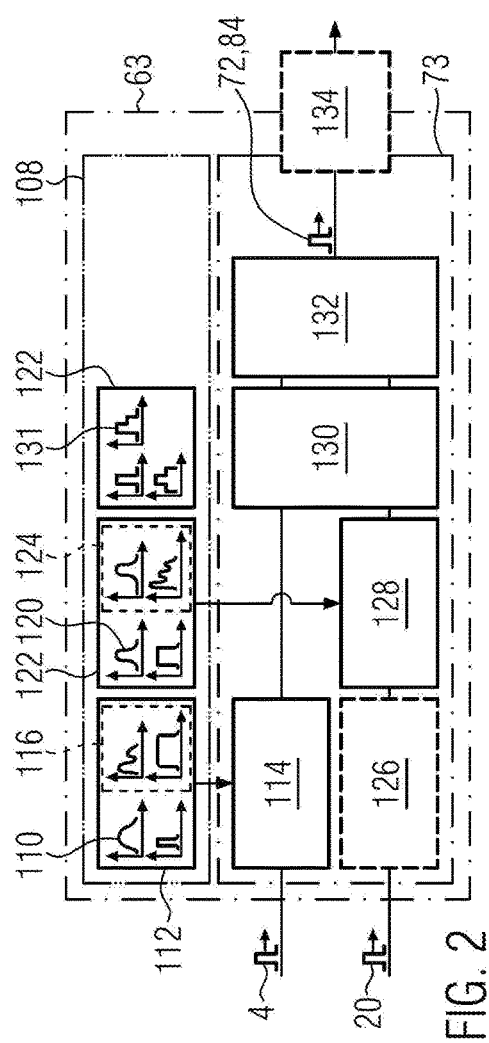
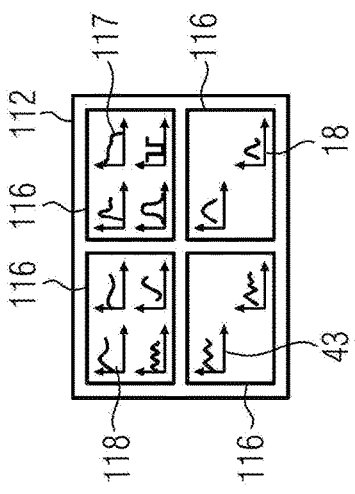
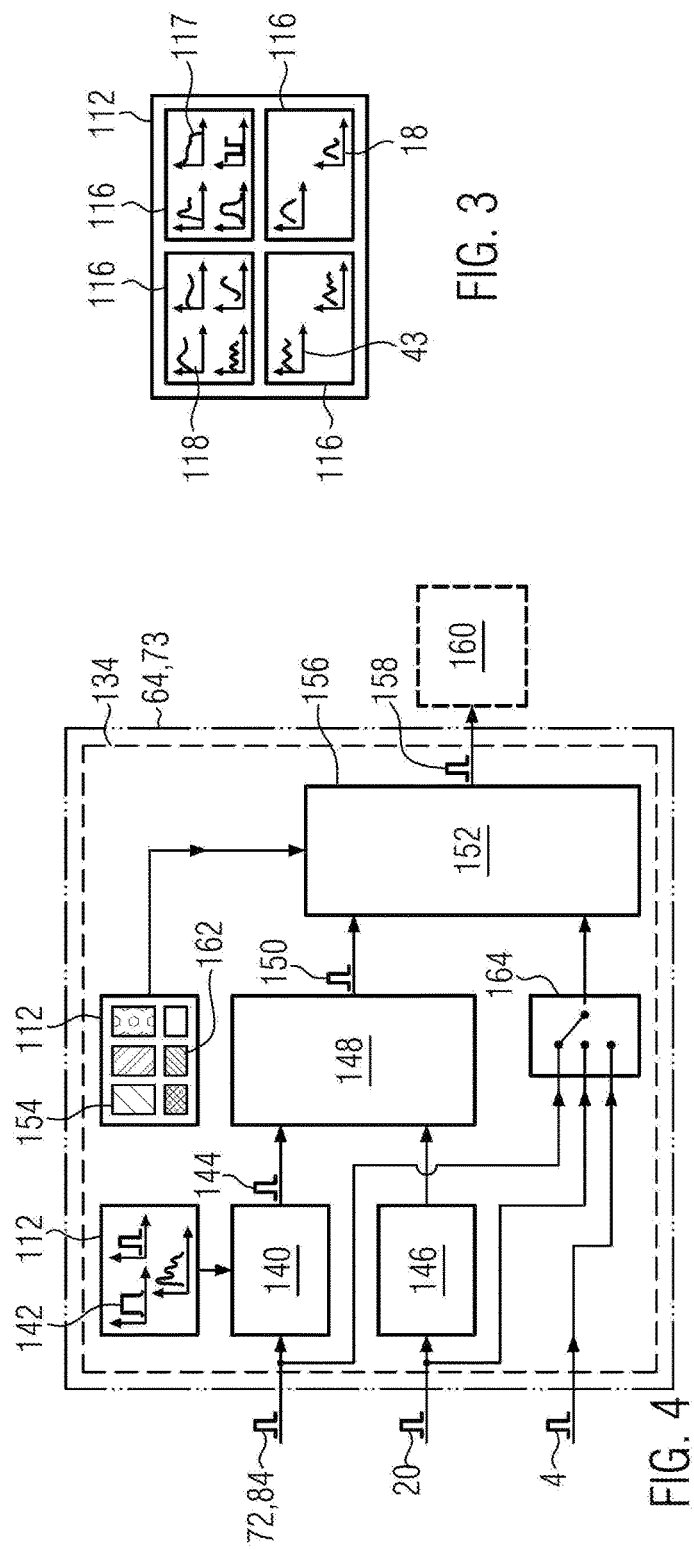

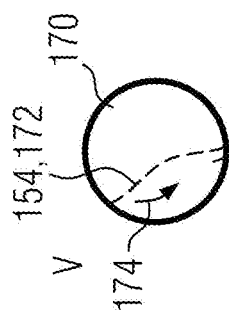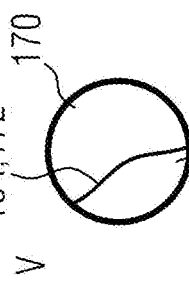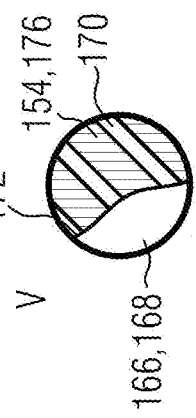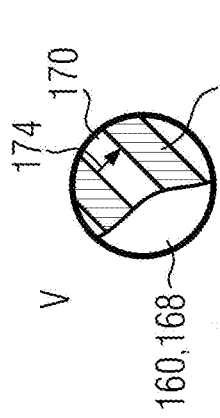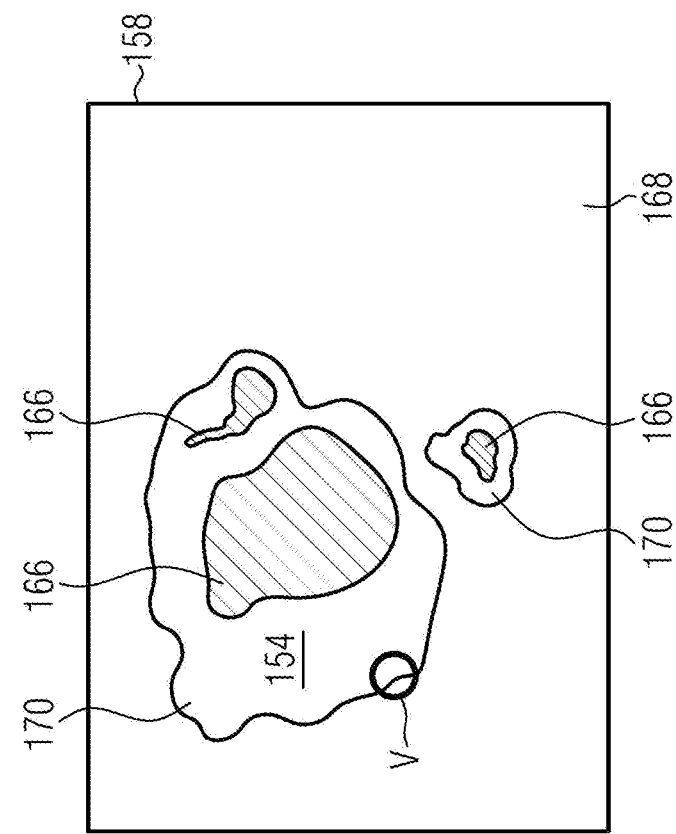

IMAGE-PROCESSING DEVICE, FLUORESCENCE OBSERVATION DEVICE AND METHOD FOR EMULATING A FIRST TYPE OF FLUORESCENCE OBSERVATION DEVICE ON A SECOND TYPE OF FLUORESCENCE OBSERVATION DEVICE

CROSS REFERENCE TO RELATED APPLICATIONS

This application claims priority of European patent application number 18215010.2 filed Dec. 21, 2018, the entire disclosure of which is incorporated by reference herein.

FIELD OF THE INVENTION

The invention relates to an image-processing device, to a fluorescence observation device comprising such an image-processing device and to a method for emulating a first type of fluorescence observation device on a second, different type of fluorescence observation device. The fluorescence observation device may in particular be a microscope or endoscope, in particular a fluorescence microscope or a fluorescence endoscope and more specifically a surgical fluorescence microscope or a surgical fluorescence endoscope.

BACKGROUND OF THE INVENTION

Fluorescence observation devices such as fluorescence microscopes and endoscopes greatly facilitate surgery and pathology. One or more fluorophores are injected into the object observed by the fluorescence observation device (here, the patient's body). Upon excitation by light in a certain spectral range, i.e. the absorption spectrum of the fluorophore, the fluorophore emits fluorescence in a fluorescence spectrum. The one or more fluorophores are designed to gather in certain types of tissue. For example, there are fluorophores which gather in a tumor, while other fluorophores gather in the bloodstream. Thus, by looking at the fluorescence spectrum, a surgeon is capable of distinguishing quickly between different types of tissue. The surgeon is thus in a better position to determine the extent of a fluorescent tumor or fluorescent vascular plexus tissue. The use of fluorescence observation devices thus greatly increases the patient's safety by preventing unnecessary tissue damage and improving removal of tumors in their entirety.

However, in order to safely use fluorescence observation devices in surgery, years of training and experience are needed. When new fluorescence technologies are developed, it is often difficult for the surgeon trained in the use of another fluorescence technology to safely handle the information provided by the new technology. The acceptance of new technology by surgeons may be impaired due to liability issues arising from a fear of being insufficiently acquainted with the new technology. Further, there is a need to provide training for a new or different fluorescence technology by building on the capabilities of other fluorescence technologies.

SUMMARY OF THE INVENTION

To solve this problem, the invention provides an image-processing device for emulating a first type of fluorescence observation device on a second, different type of fluorescence observation device, the image-processing device comprising an image processor and being configured to retrieve at least one digital fluorescence image, the at least one digital fluorescence image representing an object recorded by an image recording system of the second type of fluorescence observation device in a fluorescence spectrum of a fluorophore, the image-processing device comprising a type-emulation module, the type-emulation module being representative of an image-recording system of the first type of a fluorescence observation device, the image processor being configured to apply the type-emulation module to the at least one digital fluorescence image and to compute a digital emulated fluorescence output image from the application of the type-emulation module to the at least one digital fluorescence image, the image processing device being further configured to output the digital emulated output image.

Moreover, the invention is concerned with a fluorescence observation device, in particular fluorescence microscope or endoscope, the fluorescence observation device comprising: an image-recording system, the image-recording system being configured to record at least one digital fluorescence image in the fluorescence spectrum of a fluorophore, and an image processing device comprising an image processor and configured to receive the at least one digital fluorescence image from the image-recording system, the image-processing device comprising a type-emulation module, the type-emulation module being representative of a different image-recording system of a different type of fluorescence observation device, the image processor being configured to apply the type-emulation module to the at least one digital fluorescence image and to compute at least one digital emulated fluorescence output image from the application of the type-emulation module to the at least one digital fluorescence image, at least one display device, the at least one display device being configured to display the at least one digital emulated fluorescence output image.

Finally, the invention relates to a method for emulating a first type of fluorescence observation device on a second type of fluorescence display device, the method comprising the following steps: retrieving at least one digital fluorescence image representing an object in a fluorescence spectrum of a fluorophore and recorded by the second type of fluorescence observation device using an image-recording system computing a digital emulated output image from the at least one digital fluorescence image, and outputting the digital emulated output image for at least one of displaying or further processing, wherein the step of computing the at least one digital emulated output image comprises the step of: applying a type-emulation module to the at least one digital fluorescence image, the type-emulation module being representative of the image-recording system of the first type of a fluorescence observation device.

The type-emulation module allows the second type of fluorescence observation device to compute a digital emulated output image which corresponds to the images produced by the first type of fluorescence observation device although the first type uses a different image-recording system. The surgeon is therefore in a position to display the results in a format that he or she is used to, even if the second type of fluorescence observation device uses a different technology, in particular different hardware, to e.g. record digital fluorescence images.

The type-emulation module may be implemented as a hardware device, such as an ASIC, a CPU, an FPGA, a GPU and/or a vector processor; as a software device, e.g. a digital type-emulation module which is configured to operate on digital image data on the form of one or more subroutines; or as a combination of both a hardware and software device.

In the following, additional features, which further improve the invention, are described. The individual features can be combined independently of one another and each of the individual features is advantageous on its own. The individual features can be applied indiscriminately to the image-processing device, the fluorescence observation device and the method according to the invention.

For example, the image-processing device may be further configured to retrieve at least one digital white-light color image recorded by the second type of fluorescence observation device and representing the object illuminated by white light and to compute the digital emulated output image from a combination of the at least one digital fluorescence image to which the type-emulation module has been applied and the at least one digital white-light color image. In this embodiment, the combination of the digital white-light color image and the digital fluorescence image allows to put the fluorescing features of the object into context with non-fluorescing features which otherwise would be invisible in the digital fluorescence image.

Further, the image processor may be configured to apply the type-emulating module to the at least one digital white-light color image and to compute the digital emulated output image from a combination of the at least one digital fluorescence image to which the type-emulation module has been applied and the at least one digital white-light color image to which the type-emulation module has been applied. This allows to also emulate differences in the image recording system that affect the digital white-light images recorded by the two different types of fluorescent observation devices.

The image-recording system of the first type, which is emulated by the type-emulation module, may comprise an optical filter system which filters at least one of: fluorescence excitation light used in the first type for triggering fluorescence of the fluorophore; background illumination light used to illuminate the background of the image to make non-fluorescing areas visible; and light entering a camera system. Further, the image-recording system may comprise different types of camera. For example, the image-recording system of the first type may use only a single color camera to capture both background illumination and fluorescence simultaneously in a single digital color image, particularly in RGB format. The image-recording system of the first type may also employ a different fluorophore to generate fluorescence than the second type.

The image-recording system of the second type may comprise some or all elements of the image-recording system of the first type, the elements being different between the two types with respect to their effect on the light spectrum. For example, one or more of the light sources of the first type may have a different spectrum than that of the corresponding one or more light sources of the second type. The optical filter system of the first type may have different spectral characteristics, such as a different transmission spectrum, than that of the second type.

Further, it is advantageous if the surgeon can switch between the at least one digital emulated output image resulting from the application of the type-emulation module and a digital output image resulting from not applying the type-emulation module. Instead of applying the type-emulation module, the different image-capture and/or processing technology of the second type of fluorescence observation device may be applied. For this, the image-processing device or, equivalently, the fluorescence observation device, or the microscope or endoscope, may be configured to be selectively operated in at least two different operation modes, wherein in one of the different operation modes, application of the type-emulation module is disabled and, in another of the different operation modes, application of the type-emulation is enabled to emulate a different type of fluorescence observation device, in particular a different image-recording system. Alternatively or cumulatively, the image processing device, the fluorescence observation device, or the microscope or endoscope may be configured to be switched between at least two different operation modes, wherein, in each of the two different operation modes, a different type-emulation module is enabled and operates on the digital fluorescence image.

In another advantageous embodiment, the fluorophore used in the image-recording system to be emulated and, optionally, also used in the second type, is a fluorophore of which both the absorption spectrum and fluorescence spectrum are at least partly located in the visible-light range. In particular, the background illumination spectrum may correspond at least in part to the fluorescence absorption spectrum of the fluorophore. Thus, the background illumination spectrum may be used to trigger fluorescence of the fluorophore and as background illumination of non-fluorescent areas of the object. The background illumination color may have the same color as the absorption spectrum of the fluorophore, in particular when using a standard observer such as the standard CIE 1931 2° observer or any other standard observer as characterized by a color-matching function.

In a particular embodiment, the fluorophore is 5-ALA ppIX. 5-ALA ppIX absorbs blue light and thus, the absorption spectrum is blue and in the visible spectrum. The fluorescence spectrum is pink-red and also in the visible spectrum.

In the case of 5-ALA ppIX, where the absorption spectrum has a blue color and fluorescence is triggered by illuminating the object with blue light, respectively, the blue background illumination of the first type of fluorescence observation device may be emulated by selecting one or more blue color channels of the at least one digital white-light color image to represent the background illumination in the at least one digital emulated output image. Selecting the blue color band, or adjusting the overall color of the digital white-light color image by applying a blue digital illumination filter, closely emulates the background of the fluorescence as recorded in the first type of fluorescence observation device.

If the second type of fluorescence observation device uses a multispectral or hyperspectral camera, the digital white-light color image may have more than three color channels. In one instance, both the digital white-light color image and the at least one digital fluorescence image may be different color channels of a single digital multispectral or hyperspectral image. In such a case, the procedures are the same as for an RGB image, except that the number of color channels is different. The digital white-light color image and the digital fluorescence image are simply subsets of a single digital multispectral or hyperspectral image.

According to another embodiment, the second type of fluorescence observation device records the at least one digital white-light color image using a white-light illumination source directing illumination light onto the object. The white-light illumination source may be part of the second type of fluorescence observation device. Between the illumination source and the object, an illumination filter may be arranged to block one of fluorescence wavelengths in the fluorescence spectrum of the fluorophore and/or excitation wavelengths in the absorption spectrum of the fluorophore. The stop-band for the fluorescence wavelengths and the absorption wavelengths may be narrow-band so that the illumination is still white light.

The second type of fluorescence observation device may comprise a fluorescence excitation light source, which may be separate from or included in the white-light illumination source. The excitation light reaching the object from the excitation light source is preferably narrow-band. A fluorescence excitation filter may be arranged between the excitation light source and the object to block wavelengths other than the excitation wavelengths used for triggering fluorescence.

The second type of fluorescence observation device may further have a white-light recording filter arranged between a camera system for recording the digital white-light color image and the object. The white-light recording filter blocks or at least attenuates at least one of the excitation wavelengths and the fluorescence wavelengths. The at least one digital white-light color image preferably does not record the light used for triggering fluorescence of the fluorophore and/or emitted by the fluorescing fluorophore.

In another embodiment, the second type of fluorescence observation device may have an optical fluorescence recording filter between the object and the camera system used for recording the at least one digital fluorescence image. The fluorescence recording filter may be used in parallel to the white-light recording filter if separate cameras are used for recording the at least one digital fluorescence image and the at least one digital white-light color image. The fluorescence recording filter may have a pass band which allows only the fluorescence wavelengths to pass and blocks all other wavelengths. Thus, the at least one digital fluorescence image of the second type contains only fluorescent light, in particular if illumination containing fluorescence wavelengths has been blocked before reaching the object. Such a set-up allows the image of the object in white light to be decoupled from the fluorescence of the object, and these images to be processed separately from one another.

The information recorded by the second type of fluorescence observation device differs from the information obtained by the first type of fluorescence observation device due to the different structure of the image-recording system and the different illumination spectra used, even if the same fluorophore is employed. The type-emulation module of the second type includes information which allows mapping of the information recorded by the second type of fluorescence observation device to the information recorded by the first type of fluorescence observation device.

To enable the image-processing device to be switched between different operational modes, the image-processing device may comprise a library of different type-emulation modules, each type-emulation module being representative of a different type of fluorescence observation device or a different type of image-recording system. For example, different type-emulation modules may be used to emulate the first type of fluorescence observation device which is used with different types of fluorophores. Different type-emulation modules may also be used to emulate the effect of different light sources or illumination spectra that are used in different types of fluorescence observation devices.

According to one advantageous embodiment, the type-emulation module may contain a digital background-emulation filter, which is representative of at least one of: an illumination spectrum of a light source of the first type of fluorescence observation device; an optical illumination filter located between the light source and an observation area of the first type of fluorescence observation device; and an optical recording filter located between a camera system of the first type of fluorescence observation device. The digital background-emulation filter allows the non-fluorescing background to be rendered in the digital emulated output image as it would have been rendered by the first type of fluorescence observation device.

The digital background-emulation filter is preferably applied exclusively to the at least one digital white-light color image. The image processor may be configured to filter the at least one digital white-light color image using the background illumination filter.

The digital background emulation filter represents a fluorescence excitation spectrum of a first type of fluorescence observation device. This is particularly useful for emulating the first type of fluorescence observation device on the second type of fluorescence observation device if the fluorescence excitation spectrum generated by a light source of the first type is used to trigger fluorescence and to illuminate the background at the same time. After filtering, the at least one digital white-light color image depicts the object as it was illuminated by the fluorescence excitation spectrum in the first type of fluorescence observation device.

The first type of fluorescence observation device may comprise an optical recording filter between the observed object and a camera. The recording filter preferably has at least one pass band in the fluorescence spectrum of the fluorophore and one or more attenuation bands. The pass band allows fluorescence of the fluorophore to reach the camera. The one or more attenuation bands allow the background illumination to reach the camera at a decreased intensity compared to the at least one pass band. The one or more attenuation bands attenuate wavelengths outside the fluorescence spectrum to an intensity or brightness equal to the intensity of the fluorescence in the fluorescence spectrum. Thus, for an observer, such as the camera recording through the optical recording filter, the background illumination and the fluorescence have the same intensity, or, ideally—if a luminosity function is integrated when designing the filter arrangement—the same brightness. The digital background emulation filter may, in one embodiment, represent the filter characteristic of the optical recording filter of the first type of fluorescence observation device. Alternatively or cumulatively, a digital recording filter may be provided as part of the type-emulation module or the digital background-emulation filter. The digital recording filter represents the transfer function of the optical recording filter.

The second type of fluorescence observation device records, in one embodiment, at least one digital white-light color image of the object and at least one digital fluorescence image. The digital fluorescence image is preferably a digital monochrome image, but may also be a digital color image, i.e. may comprise a plurality of digital monochrome images, each representing a different color channel.

In particular, the second type of fluorescence observation device preferably does not have background illumination in the fluorescence excitation spectrum. Instead, the second type of fluorescence observation device may provide a white-light image rendering the object in its natural colors. According to one aspect, the image-processing device emulates the background illumination in the excitation spectrum of the first type by applying the type-emulation module, in particular the digital background emulation filter, to the at least one digital white-light color image.

If the absorption spectrum of the fluorophore or the background illumination spectrum of the first type of fluorescence observation device has a color which corresponds to one color channel of a color space of the digital white-light color image, then this color of the color channel may be selected to represent the background illumination of the first type. For example, if the digital white-light color image is recorded by an RGB camera, and is thus in the RGB color space, and the fluorescence absorption spectrum—or the fluorescence excitation spectrum used for triggering fluorescence in the first type of fluorescence observation device—of the fluorophore has a green color, then the green color channel of the RGB digital white-light color image may be used to represent the object as recorded in the background illumination of the first type. This is particularly advantageous if the white-light color image comprises different color channels which can be processed independently of one another. Selecting or extracting a single color channel results in a faster processing speed than applying a digital filter such as the digital illumination filter to more than one color channel. In this case, the type-emulation module, in particular the background emulation filter, may contain a digital mask to eliminate those color channels of the at least one digital white-light color image that are not present or do not contribute beyond a predetermined threshold to the background illumination of the first type. If one or a subset of the available color channels of the at least one digital white-light color image is used as the color band to which the background illumination color is assigned, the digital background illumination filter may be used to adjust the intensity or brightness of this one or more color channel.

The image processor may be configured to apply the digital background illumination filter to the at least one digital white-light color image and/or to select one or more predefined color channels of the at least one digital white-light color image for inclusion in the at least one digital emulated output image.

The type-emulation module may contain a library of different digital background-emulation filters that are representative of different types of fluorescence observation device, image-recording systems and/or, particularly, optical components thereof.

The digital background-emulation filter may, in another embodiment, contain at least one of: at least one or more digital light-source filters representative of the spectrum of the light source of a first type of fluorescence observation device; one or more digital illumination filters representative of an optical filter located between the light source and an observation area of the first type of fluorescence observation device; and one or more digital recording filters representative of an optical recording filter located between a camera system and the observation area of the first type of fluorescence observation device.

The digital background-emulation filter may be computed by combining, e.g. multiplying in the spectral domain, at least two of the list containing at least one digital light-source filter, at least one digital illumination filter and at least one digital recording filter. The modular design of the digital background-emulation filter allows different types or setups of fluorescence observation devices to be easily emulated on the second type. The digital background-emulation filter, digital light-source filter, digital illumination filter and/or digital recording filter may be selectable by a user, for example via a graphical user interface of the second type of observation device. The user may thus put together the first type of fluorescence observation device that he or she wishes to emulate on the second type of observation device by selecting its digital representation on the second type of fluorescence observation device. The type-emulation module may also be selected from a library by the user via a graphical user interface in order to switch quickly between different types of fluorescence observation devices.

In another embodiment, the type-emulation module comprises a digital fluorescence-emulation filter, which is representative of at least one of the fluorescence spectrum of the fluorophore and an optical recording filter located between the camera system of the first type and the observation area of the first type. The digital fluorescence-emulation filter is used to emulate the fluorescence spectrum recorded by the first type of fluorescence observation device. The digital fluorescence-emulation filter is preferably applied exclusively to the at least one digital fluorescence image. The image processor may be configured to apply the digital fluorescence-emulation filter to the at least one digital fluorescence image.

A modular design of the digital fluorescence-emulation filter may be preferred. In such a design, the digital fluorescence-emulation filter may contain at least one of: one or more digital fluorescence-emission filters representative of a fluorescence spectrum of a fluorophore; and one or more digital recording filters representative of an optical recording filter located between a camera system and the observation area of the first type of fluorescence observation device. In particular, the optical recording filter emulated by the digital recording filter may have a pass band which is located in the fluorescence spectrum of the fluorophore or overlaps with a pass band of the digital fluorescence filter. The digital recording filter is the digital background-emulation filter and the digital fluorescence-emulation filter may be the same.

The type-emulation filter may contain a library of digital fluorescence-emulation filters that are representative of different types of fluorescence observation devices, optical recording filters and/or fluorophores. Again, such a library allows different types of fluorescence observation devices to be selected and emulated on the second type of observation device.

The first and second types of fluorescence observation devices may also differ in terms of the relative intensity or, if the luminosity function is taken into account, the relative brightness of the non-fluorescing background, on the one hand, represented in the second type by the at least one digital white-light color image, and the fluorescing sections of the image, on the other, represented in the second type by the at least one digital fluorescence image. To adjust the relative intensities, or the relative brightness, of background and fluorescence in the second type of fluorescence observation device to correspond to the first type of fluorescence observation device, the type-emulation module may comprise a digital attenuation filter for adjusting at least one of the mean intensity or brightness of the digital white-light input image and the mean intensity or brightness of the digital fluorescence input image relative to one another in order to e.g. obtain a predetermined ratio. Preferably, the mean intensity or brightness is adjusted after application of at least one of the digital background-emulation filter and the digital fluorescence emulation filter. The intensity or brightness of the at least one digital fluorescence input image and the at least one digital white-light color image is preferably determined by computing the mean intensity. The mean intensity or brightness may be computed using an arithmetic or geometric mean across the entire image. The brightness may be computed from the intensity using a luminosity function such as the CIE 1931 2° standard.

The image processor may be configured to compute the digital fluorescence-emulation filter from the digital fluorescence filter and the digital recording filter, e.g. by a multiplication in the spectral domain.

The image-processing device or the image processor may comprise a graphical user interface which allows a user to choose between different digital fluorescence-emulation filters, digital fluorescence-emission filters and/or digital recording filters.

In order to facilitate the changeover in technology from the first type of fluorescence observation device to the second type of observation device, and for schooling purposes, it is preferred that, in another embodiment, the difference between a digital color output image generated using the second type of fluorescence observation device, i.e. without using the type-emulation module, and a digital color output image generated by the first type of fluorescence observation device, i.e. with using the type-emulation module, is computed. Preferably, the difference is marked in a digital difference image in one mode of operation of the second type of fluorescence observation device.

The digital difference image is preferably a color image and computed from the digital emulated output image and/or the at least one digital fluorescence image. The visual marking of the difference allows the surgeon's attention to be drawn to fluorescent areas which would otherwise not be displayed in the digital emulated output image as they would not have been visible in the images generated by the first type. To create such a marking, a pattern generator may be provided in the digital image-processing device, in particular in the type-emulation module, for generating a digital image pattern in the digital difference image. The pattern generator may further comprise at least one representation of a pseudo-color and be adapted to assign the pseudo-color to the at least one pattern.

The digital image pattern may be generated, according to one aspect of a digital difference image, in an area where the at least one digital emulated output image as computed using the type-emulation module differs from the at least one digital emulated output image that is computed without using the type-emulation module.

According to another aspect, a digital fluorescence extraction filter may be provided. The digital fluorescence extraction filter is configured to extract the fluorescence of the at least one fluorophore as recorded in the first type. The digital fluorescence extraction filter may correspond to the digital fluorescence-emulation filter. Application of digital fluorescence extraction filter to a digital fluorescence image may directly result in the digital difference image. Filtering the digital fluorescence image may be computationally more efficient than filtering the digital emulated output image, especially if the at least one digital fluorescence image is a monochrome image or, generally, contains fewer color channels than the digital emulated output image.

The image processor may be configured to compute this difference and assign the digital image pattern to areas where the difference exceeds a certain threshold. It is preferred that the area has an adjustable minimum size, such as 5×5 pixels. The pattern may be temporally and/or spatially varying or comprise a field of (constant) pseudo-color. The pattern generator may, in another embodiment, be adapted to assign a fluorescence pseudo-color, which may be selected by the user or is selected to correspond to the spectrum of the fluorescence-emulation filter.

A spatially varying pattern may e.g. be a hatching. A temporally varying pattern may be an animated pattern, e.g. a blinking pattern which is enabled and disabled in subsequently generated digital difference output images.

The image processor may, in particular, be adapted to compute the digital emulated output image or the digital difference image by merging the at least one digital white-light color image, either in a processed or in an unprocessed state, with the at least one digital fluorescence image, also either in a processed or in an unprocessed state, using the algorithm disclosed in EP 3 205 254 A1. Alternatively, the at least one digital fluorescence image may be converted into a grayscale color image if it is not already in this format. Then, the digital fluorescence emulation filter may be applied by e.g. the image processor to transform the grayscale color image into a color image representing the fluorescence spectrum of the fluorophore.

The invention further relates to a fluorescence observation device comprising an image-processing device in any of the above embodiments, the fluorescence observation device being of the second type. The fluorescence observation device may, in particular, comprise a camera system being configured to record the at least one digital white-light color image and the at least one digital fluorescence image, preferably simultaneously. The fluorescence observation device may comprise separate cameras for recording the at least one digital white-light color image and the at least one digital fluorescence image, or a single camera, such as a multispectral or hyperspectral camera, for recording the at least one digital white-light color image and the at least one digital fluorescence image in more than three color channels. If separate cameras are used, an RGB camera may be comprised in the fluorescence observation device for capturing the at least one digital white-light color image. A separate monochrome, IR, NIR or RGB camera may be used for capturing the at least one digital fluorescence image. Filter systems, such as the white-light and the fluorescence recording filter as described above, may be included.

If separate cameras are used, the image processor may be configured to spatially match the at least one digital white-light image and the at least one digital fluorescence image so that identical features are located at identical positions and have the same form in both the at least one digital white-light image and the at least one preferably simultaneously recorded digital fluorescence image.

Finally, the invention also relates to a computer program, a computer program product and/or a non-transitory computer-readable medium storing a computer program, the computer program causing a computer in a fluorescence observation device, or a fluorescence microscope or endoscope to execute the method in any of the embodiments described above.

BRIEF DESCRIPTION OF THE DRAWING VIEWS

In the figures:

FIG. 2 shows a schematic representation of the processing steps of an image-processing method according to the invention;

FIG. 3 shows a schematic representation of a library of type-emulation modules;

FIG. 4 shows a schematic representation of a further processing step;

FIG. 5 shows a schematic representation of a digital difference image in which a difference in the image output images of different types of fluorescence microscopes or endoscopes has been automatically marked with digital image pattern; and FIGS. 6A to 6D show schematic renditions of digital image patterns.

DETAILED DESCRIPTION OF THE INVENTION

Figure 1:
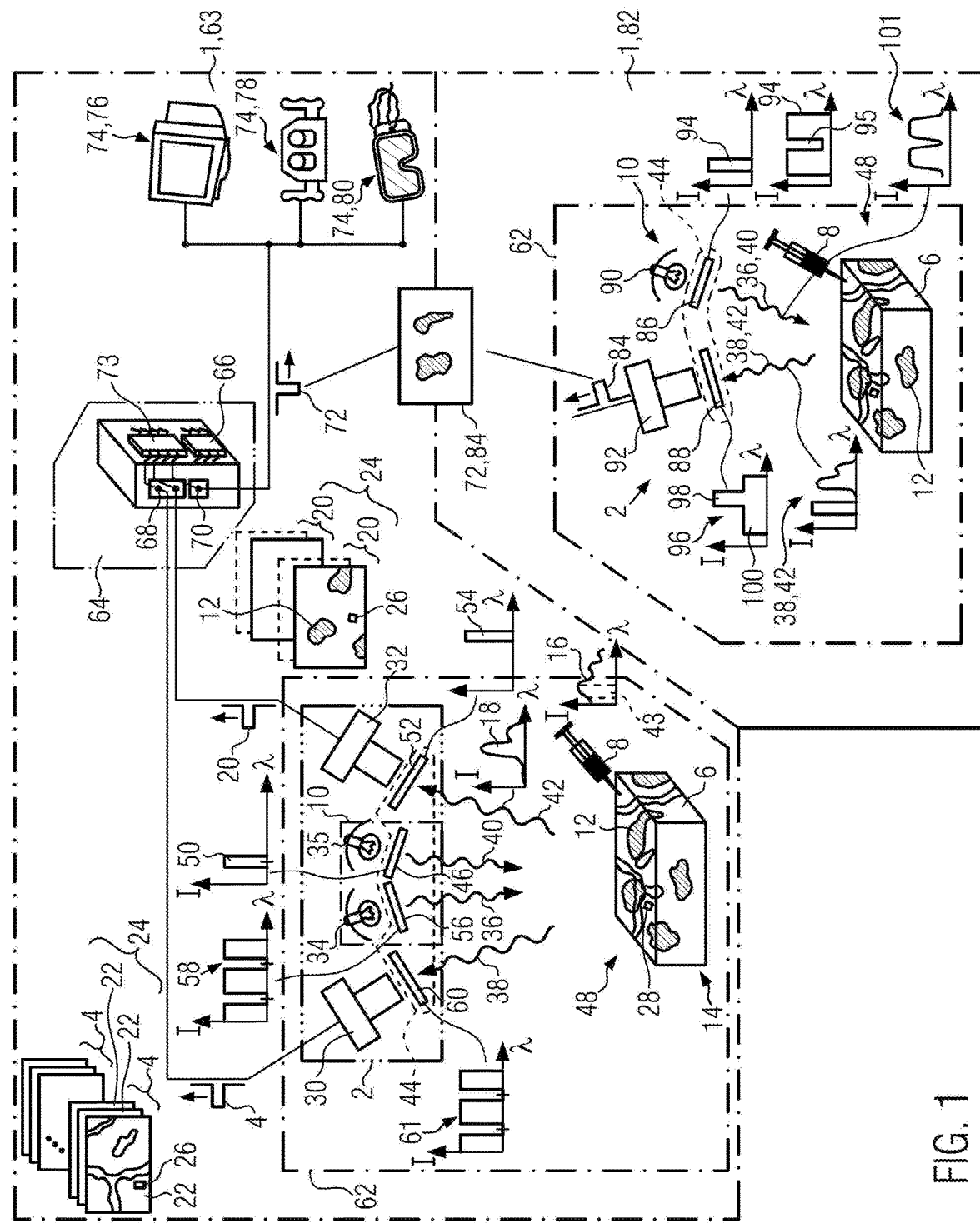
FIG. 1 shows a schematic representation of a fluorescence observation device, such as a fluorescence microscope or endoscope according to the invention.

First, the structure and function of a fluorescence observation device 1 is described with reference to FIG. 1. For exemplary purposes, the fluorescence observation device 1 of FIG. 1 is a fluorescence microscope, in particular a fluorescence surgical microscope. It may alternatively be a fluorescence endoscope, in particular a surgical fluorescence microscope, to which the following description is also applicable.

The fluorescence microscope or endoscope 1 may comprise a camera system 2. The camera system 2 is configured to record at least one digital white-light color image 4 of an object 6, which may in particular be live tissue, such as live tissue of a patient undergoing surgery or a cell that is e.g. undergoing biopsy. The object 6 has been provided with one or more fluorophores 8 or otherwise contains one or more fluorophores 8. The camera system 2 may be stereoscopic or holographic. The resulting images may be recorded in a corresponding data format, i.e. a two-dimensional, stereoscopic, three-dimensional or holographic data format.

The fluorescence microscope or endoscope 1 may further comprise an illumination system 10 for illuminating the object 6. Upon illumination within a certain spectral range, the fluorophore 8 starts to emit fluorescence. Areas 12 which exhibit a concentration of the fluorophore 8 emit fluorescence at a higher intensity than areas in which there is a low density of the fluorophore 8. Where there is no fluorophore 8 at all, no fluorescence will be emitted.

The fluorophore 8 is preferably configured to attach to certain predefined chemical compounds in the live tissue 14. These predefined chemical compounds are selected as being typical of a certain type of live tissue 14, for example tumorous tissue or blood. The fluorophore 8 will therefore gather in live tissue 14 containing the appropriate chemical compounds. This type of tissue will then exhibit a high density of the fluorophore 8 and thus, upon illumination in an absorption spectrum 16 of the fluorophore, be visible as a fluorescent area 12. The absorption spectrum 16 of the fluorophore consists of those wavelengths $\lambda$ of illumination light that will trigger fluorescence. By contrast, the fluorescence spectrum 18 consists of those wavelengths $\lambda$ in which fluorescence is emitted by the fluorophore.

If different types of tissue are to be marked by different fluorescent colors in order to be distinguished from one another visually, more than one fluorophore 8 may be used in the object 6. In this case, the absorption spectra 16 and the fluorescence spectra 18 of the different fluorophores should have non-overlapping areas so as to be able to selectively and/or separately trigger and/or record the fluorescence of the different fluorophores.

The intensity distribution of the fluorescence of the fluorophore 8 allows the type of tissue to be identified by looking at an image recorded in the fluorescence spectrum 16. For this, the camera system 2 is configured to record at least one digital fluorescence image 20 of the fluorescing fluorophore 8 in at least part of the fluorescence spectrum 18.

The digital fluorescence image 20 may be a monochrome (e.g. grayscale) image according to one embodiment. According to another embodiment, the digital fluorescence image 20 may be a color image like the digital white-light color image 4.

A color image may comprise a plurality of monochrome images 22. Each monochrome image represents a different color channel. The color channels are selected to be able to represent natural colors and white light. If, for example, the digital white-light color image 4 is in an RGB format, three monochrome images 22 are comprised by one color image. Each monochrome image 22 corresponds to one color channel, i.e. one monochrome image corresponds to the red R color channel, one monochrome image corresponds to the green G color channel and one monochrome images corresponds to the blue B color channel. The digital white-light color image 4 and the digital fluorescence image 20 may also be part of a digital color image which has more than three color channels. Such a digital multispectral or hyperspectral color image may be recorded if the camera system 2 comprises a multispectral or hyperspectral camera which simultaneously records more than three color channels.

Both the digital white-light color image 4 and the digital fluorescence image 20 may be part of a time series 24 of subsequent images, e.g. a video. Further, each image 4, 20 may result from an image-processing operation which includes more than one digital input image. For instance, the digital white-light color image 4 and/or the digital fluorescence image 20 may be an HDR image. An HDR image has increased contrast and has been computed from a series of digital images recorded at different exposure levels.

Each digital image 4, 20 comprises a plurality of pixels 26. Each pixel 26 in an image 4, 20 corresponds to the same location 28 of the object 6.

In the embodiment shown in FIG. 1, the camera system 2 comprises two cameras 30, 32. An RGB camera 30 is used for recording the digital white-light color images 4. A fluorescence camera 32, which may be an RGB camera or a monochrome camera such as a black and white camera, an IR camera, an NIR camera or a UV camera, is used for recording the at least one digital fluorescence image 20.

If different cameras 30, 32 are used, it cannot be guaranteed that all cameras have the same viewing angle, magnification and field of view onto the object 6. Therefore, the at least one digital white-light color image 4 and the at least digital fluorescence image 20 may be matched to one another using a matching algorithm. After matching, the features of the object 6, such as the fluorescent areas 12, are all at the same position and of the same size, form and orientation in the at least one digital white-light color image 4 and the at least one digital fluorescence image 20.

The illumination system 10 may comprise one or more light sources, for example two light sources 34, 35. One light source 34 may be used to generate background illumination light 36 which is directed onto the object 6. Preferably, the background illumination light 36 is in the visible-light range, broadband and, in particular, white light. The at least one digital white-light color image 4 is recorded at least primarily, preferably exclusively, using the background illumination light 36. The at least one digital white-light color image 4 renders the object 6 preferably in its natural colors by recording the background illumination light 36 reflected off the object 6. The reflected background light is indicated by reference numeral 38 in FIG. 1.

In order to decouple the image capture of the object 6 in its natural visible colors from the image capture of the at least one fluorescing fluorophore, the second light source 35 may be used. The second light source 35 is a fluorescence excitation light source which emits fluorescence excitation light, which is also directed onto the object 6. The fluorescence excitation light 40 preferably only contains wavelengths $\lambda$ which are in the absorption spectrum 16 of the at least fluorophore 8. For separating the information contained in the background illumination from the information in the fluorescence, the fluorescence excitation light 40 preferably exclusively serves to trigger fluorescence but not to illuminate the object 6. The fluorescence excitation light 40 is absorbed by the fluorophore 8, which then emits fluorescence light 42, which in turn is captured by the camera system 2 in the at least one digital fluorescence image 20. The excitation spectrum 43 of the fluorescence excitation light 40 does not need to correspond to the absorption spectrum 16, but can merely comprise a subset of the wavelengths λ in the absorption spectrum 16. In particular, the excitation spectrum 43 may be narrow-band.

Although two separate light sources 34, 35 are shown in FIG. 1, a single, e.g. tunable, light source may be used instead. Moreover, although it is preferred that the at least one digital white-light color image 4 and the at least one fluorescence image 20 are recorded simultaneously, they can also be recorded sequentially by the camera system 2. In such a sequential case, the illumination system 10 may alternatingly generate background illumination light 26 and fluorescence excitation light 40, and the camera system may—synchronously with the generation of the respective illumination light—sequentially record at least one digital white-light color image 4 and at least one digital fluorescence image 20.

To be able to process the information contained in the digital white-light color image 4, on the one hand, and the digital fluorescence image 20, on the other, cross-talk between the different images should be minimized. For this, the fluorescence microscope or endoscope 1 may comprise an optical filter system 44. The optical filter system 44 makes sure that there is no or minimum overlap between the information that is recorded in the at least one digital white-light color image 4 and the at least one digital fluorescence image 20. This is achieved by separating the wavelengths recorded in the two respective images 4, 20; i.e. in each of the images 4, 20, different spectral ranges are recorded. This is explained in the following:

The filter system 44 comprises an optical fluorescence excitation filter 46, which is arranged between the illumination system 10 and the object 6 or, more preferably, an observation area 48 in which objects 6 to be observed by the fluorescence microscope or endoscope 1 are placed. The fluorescence excitation filter 46 is preferably a narrow-band pass-band filter having a fluorescence excitation pass band 50 which is located in the absorption spectrum 16. Thus, the fluorescence excitation light 40 is limited to containing only wavelengths that fall within the fluorescence excitation pass band 50. If the light source 35 is already narrow-band, the optical fluorescence excitation filter may be omitted. In both cases, the fluorescence excitation light 40 has a narrow-band fluorescence excitation spectrum 43.

An optical fluorescence emission filter 52 is located between the observation area 48 and the camera system 2. The optical filter 52 is preferably a narrow-band pass-band filter having a fluorescence emission pass band 54 which is located in the fluorescence spectrum 18 of the at least one fluorophore 8. Different fluorescence cameras 32 for simultaneously recording the fluorescence of different fluorophores 8 may use different fluorescence emission pass bands 54 and different fluorescence emission filters 52, respectively. Thus, the light recorded in the at least one digital fluorescence image 20 is restricted to wavelengths contained within the fluorescence emission pass band 54.

The filter system 44 may further comprise a background illumination filter 56, which is preferably a band-stop filter having at least one stop band which is preferably narrow-band. In particular, the one or more stop bands of the background illumination filter 56 may correspond to the one or more fluorescence excitation pass bands 50 of the optical filter system 44. The background illumination filter 56 may further comprise a stop band which corresponds to the one or more fluorescence emission pass bands 54 of the filter system 44. The filter characteristic of a background illumination filter 56 is indicated by reference numeral 58 in FIG. 1. The background illumination filter 56 is arranged between the illumination system 10 and the observation area 48.

Blocking the fluorescence excitation pass band 50 for the background illumination light prevents inadvertently triggering fluorescence of the fluorophore 8. Fluorescence in this case is selectively triggered only if the fluorescence excitation light 40 is generated using e.g. the fluorescence illumination source 35. If such a selective triggering of fluorescence is not needed, the background illumination filter 56 does not need to block the fluorescence excitation pass band 50.

Finally, the filter system 44 may comprise a white-light recording filter 60 which is arranged between the camera system 2 and the observation area 48. The filter characteristic 61 of the white-light recording filter 60 is schematically depicted as reference numeral 62 in FIG. 1. The white-light recording filter 60 is preferably a band-stop filter having at least one stop band which coincides with the fluorescence excitation pass band 50 and/or the fluorescence emission pass band 54 for the reasons explained above in connection with the background illumination filter 56.

A stop band of the background illumination system 56 which corresponds to the fluorescence emission pass band 54 may be necessary if the fluorescence emitted by the fluorophore 8 should not be recorded in the at least one digital white-light color image 4. Such a stop band may not be necessary if the intensity of the fluorescence emitted by the fluorophore 8 is so weak compared to the background illumination that it can be neglected in the at least one digital white-light color image 4. Thus, the background illumination filter 56 is optional. The pass bands and the corresponding stop bands are preferably narrow-band so that the white-light character of the reflected background illumination light is maintained.

With the arrangement described above, the fluorescence microscope or endoscope 1 records the information in the visible-light spectrum, without any information on fluorescence in the at least one digital white-light color image 4 and the information about the at least one fluorescing fluorophore 8, without any information on the background illumination in the at least one digital fluorescence image 20. The camera system 2, the at least one fluorophore 8 and the optical filter system 44 are part of the image recording system 62 and thus the type 63 of the fluorescence microscope or endoscope 1. Different types of fluorescence microscopes or endoscopes use different image-recording systems.

The fluorescence microscope or endoscope 1 further comprises an image-processing device 64. The image-processing device 64 is configured to retrieve the at least one digital white-light color image 4 and the at least one digital fluorescence image 20 either directly from a camera system 2 or from a stationary or mobile memory section such as a storage section 66. The storage section 66 may comprise a disk, RAM or ROM memory, or a cloud device for storage.

The image-processing device 64 may comprise an input section 68 to which a camera system 2 or a storage section 66 may be connected. The input section 68 may be wireless or wire-based, or a combination of both. Various data transmission protocols may be comprised by the input section 68, as long as the data transfer protocols are usable for transmitting single or time series of digital images. Examples of suitable protocols are streaming connections on the internet, or HDMI, DVI, USB or RGB connections.

Likewise, the image-processing device 64 may comprise an output section 70 for outputting a digital emulated output image 72. The output section 70 may use any of the protocols described above in connection with the input section 68, which output protocol is suitable for transmitting digital images or videos.

The image-processing device is configured to compute the at least one digital emulated output image 72 from the at least one digital white-light color image 4 and the at least one digital fluorescence image 20. For this, the image-processing device 64 may comprise an image processor 73, which may be hardware, software or a combination of both. For example, the image processor 73 may comprise at least one CPU, FPU, FGPA, vector processor, GPU or an ASIC for executing software. The image processor 73 may comprise subroutines which run on such a hardware device and modify its internal structure, e.g. by modifying the switching state of electronic structures, when executed.

The digital emulated output image 72 may be further processed or displayed on a display device 74, such as a monitor 76, an eyepiece 78 or AR or VR goggles 80. The display device 74 may be part of the fluorescence microscope or endoscope 1.

According to the present invention, the image processor 73 is configured to compute the digital emulated output image 72 such that it corresponds to the digital emulated output image 72 recorded by another type 82 of fluorescence microscope or endoscope 1 having a different hardware structure, such as an image recording system 62, in particular a different camera system 2, a different illumination system 10 and/or a different optical filter system 44. The image-processing device 64, or the type 63 of fluorescence microscope or endoscope 1, is thus configured to emulate the type 82 having different optical hardware.

In FIG. 1, the situation is shown where the different type 82 of microscope or endoscope observes the same object 6 with the same fluorophore 8, resulting the same field of view and the same fluorescent areas 12. This structure is emulated by the type 63.

In contrast to the camera system 2 of the type 63, the camera system 2 of the type 82 records a single digital color output image 84 in which the fluorescence excitation light 40 is also used as the background illumination light 36. The camera system 2 records the background illumination light 36 and the fluorescence light 42 in the single digital color output image 84. For this, the optical filter system 44 may comprise at least one of an illumination filter 86 arranged between the illumination system 10 and the observation area 48 and an optical recording filter 88 arranged between the camera system 2 and the observation area 48.

Moreover, the illumination system 10 may comprise only a single light source 90 which serves as a light source for both the background illumination light 36 and the fluorescence excitation light 46.

The camera system 2 may, in particular, comprise a single color camera 92 which may, be an RGB camera, but may also be a multispectral or hyperspectral camera. It further may be a two-dimensional, stereoscopic, three-dimensional or holographic camera system.

The optical illumination filter 86 is optional and may comprise or consist of an optical pass band filter having a pass band 94 which may be narrow-band or broadband, and may include wavelengths within the absorption spectrum 16 of the fluorophore 8 in addition to any other wavelengths for illuminating the object 6 in the absorption spectrum 16. Alternatively or in addition, the illumination filter 86 may have a stop band 95 in a wavelength range falling within the fluorescence spectrum 18 of the fluorophore 8, thus preventing illumination of the object 6 with light that may be emitted as fluorescence by the fluorophore 8.

The optical recording filter 88 may be adapted to equalize the intensity—or, if a luminosity function is included, the brightness—of the light in the fluorescence spectrum 18 of the fluorophore 8 and the reflected background illumination light 39. With the illumination filter 86, the light in the background, i.e. the light not included in the fluorescence spectrum 18 of the fluorophore 8, is attenuated to match the intensity of the fluorescence. Thus, the optical recording filter 88 has a filter characteristic 96 in which wavelengths λ in a pass band 98 in the fluorescence spectrum of the fluorophore 8 are less attenuated than wavelengths λ outside this band and in the pass band of the illumination filter 86. The pass band 98 and the bands with higher attenuation may be part of an attenuation band 100 of the optical recording filter 88 which is restricted to the spectral range of the background illumination light 36 and the fluorescence excitation light 40. The illumination filter 86 may have a pass band which matches the pass band 100. The pass band 98 may correspond to a stop band 25 of the illumination filter 86.

The type 82 of fluorescence microscope of endoscope thus produces a single digital color output image 84 which contains both information on the background and information on fluorescence.

The image-processing device 64 of the fluorescence microscope or endoscope 1 is configured to compute the digital emulated output image 72 from the at least one digital white-light color image 4 and the at least one digital fluorescence image 20 such that it corresponds to the digital color output image 84 of the type 82, especially if the same fluorophore 8 is used. Preferably, the type 82 uses a fluorophore 8 in which both the absorption spectrum 16 and the fluorescence spectrum 18 are in the visible-light range, so that the fluorescence excitation light 40 may double as background illumination light 36 having the background illumination spectrum 101.

One example of such a fluorophore is 5-ALA ppIX. For this fluorophore, the absorption spectrum 18 is blue. Thus, blue light may be used both to trigger fluorescence and to illuminate the background. The fluorescence spectrum 18 of 5-ALA ppIX is pink. Thus, the resulting digital color output image 84 of the type 82 of microscope or endoscope using 5-ALA ppIX as a fluorophore will result in a pink and blue image. The stop band 95 and the pass band 98 match the pink color; the pass bands 94 and 100 match the blue excitation and background illumination color.

The fluorescence microscope or endoscope 1 of the type 63, in particular its image-processing device 64, may use a fluorophore 8 other than the one used by the type 82, and to compute a digital emulated output image 72 which corresponds to the digital color output image 84 that would have been recorded by the type 82 using this other fluorophore with its different absorption and emission characteristics. The only pre-condition for emulating such an operation of the type 82 of fluorescence microscope or endoscope 1 is that the two different fluorophores 8 bind to the same type of tissue, i.e. that the type of tissue marked by the different fluorophores 8 correspond to one another.

The emulation performed on the fluorescence microscope or endoscope 1 is further explained with reference to FIGS. 2 and 3.

In order to emulate the type 82 on the fluorescence microscope or endoscope 1, the image-processing device 64 comprises a type-emulation module 108 which may reside as software in the storage section 66, be a hardware device, such as an ASIC, FGPA, GPU or CPU of the image processor, or comprise both hardware and software. The type-emulation module 108 comprises functions, in particular digital filters, that are configured to operate on at least one of the at least one digital white-light color image 4 and the at least one digital fluorescence image 20 for emulating the digital color output image 84 as it would have been generated by the type 82. The type-emulation module 108 represents the image-recording system 62 of the type 82, such as the spectra of the light 36, 40 incident on the object 6; the type of camera system 2, such as the type of color camera 92; the characteristics of the fluorophore 8 used in the type 82, such as its absorption spectrum 16 and it fluorescence spectrum 18; and the structure and components of the filter system 44. Preferably, the at least one digital white-light image 4 and the at least one digital fluorescence image 20 are normalized and, optionally, homogenized and/or deconvoluted prior to application of the type-emulation module 108.

The effect of the different optical filter systems 44 of the type 82 and the different illumination spectrum used by this type, as well as the different emission spectrum of a possibly different fluorophore 8 are taken into account in that the image-processing device 64 comprises at least one digital background-emulation filter 110, preferably a library 112 comprising a plurality of digital background-emulation filters 110.

The digital background-emulation filter 110 represents the components of the light recorded by the camera system 2 of type 82, i.e. the spectrum or color by which the non-fluorescing background of the at least one digital output color image 84 would be illuminated. The digital background-emulation filter 110 is applied to the at least one digital white-light color image 4 in a step 114. For example, if blue light having a certain spectrum is used to both illuminate the object 6 and trigger fluorescence of the fluorophore 8, a digital background-emulation filter 110 is used which corresponds to the spectrum of this blue light. After this filtering process, the image rendered by the now modified digital white-light color image 4 is tinted as if the object 6 in the observation area 48 of the fluorescence microscope or endoscope 1 had been illuminated with the same type of blue light as the type 82.

The filtering process may be done by carrying out spectral filtering, i.e. computing a convolution or spectral multiplication of a filter function with the digital white-light color image 4. As this may be computationally expensive if high-resolution images are used that are received at a high frame rate, the filtering process may comprise a simple weighing of the monochrome images 22 of the digital white-light color image 4. For example, if the type 82 has used blue light to illuminate the object 6 and triggering fluorescence, the monochrome images 22 of the green and red color channels in an RGB image may simply be set to zero or attenuated, as defined by the digital background-emulation filter 110.

In a variant of the type-emulation module 108, the library 112 of digital background-emulation filters 110 may comprise one or more sub-libraries 116, where each sub-library represents variants of a different component of the image-recording system 62 (FIG. 3). One sub-library 116 may contain various digital illumination filters 117. Another sub-library 116 may contain digital representations of different fluorescence excitation spectra 45 emitted by the light source 90 of the type 82, or generated by the optical fluorescence excitation filter 46. Another sub-library 116 may comprise digital representations of fluorescence spectra 18 of different fluorophores 8. Another sub-library 116 may comprise different digital recording filters 118. Another sub-library 116 may comprise digital filters representing different spectral responsivities of different cameras 92 of the type 82. Preferably, each of the digital filters contained in the various sub-libraries 116 is individually selectable by a user of the fluorescence microscope or endoscope 1, or is automatically selected by the fluorescence microscope or endoscope 1 if a type 82 is selected by the user. The resulting digital background-emulation filter 110 is then simply computed by combining the different filters from the various sub-libraries 116. For example, the digital background-emulation filter 110 may be computed by multiplying, in the frequency or spectral domain, the digital representation of spectra of the light source 90, the digital illumination filter 117, the digital recording filter 118, the digital representation of the fluorescence spectrum 18 and the spectral responsivities of the camera 92 to arrive at a type-emulation module which accurately represents the image recording system 62.

The type-emulation module 108 may further comprise a digital fluorescence emulation filter 120 or a library 122 containing a plurality of digital fluorescence emulation filters 120. The digital fluorescence emulation filter 120 is used to assign the digital fluorescence image 20 a color which corresponds to the color recorded in the digital color output image 84 of the type 82 from the fluorescing fluorophore 8. In the library 122 of digital fluorescence emulation filters 120, one or more sub-libraries 124 may be contained. One sub-library 124 may comprise filter functions emulating the fluorescence spectrum 18 of the fluorophore 8. Another sub-library 124 may emulate the effect of the illumination filter 86 on the fluorescence spectrum 18. Another sub-library 124 may contain one or more digital illumination filters which emulate the spectrum of the light source 90. Another sub-library 124 may contain one or more digital light source filters which emulate the optical recording filter 88. Another sub-library 124 may contain one or more digital filters representing the spectral responsivities of the camera system 2 or the camera 92 of type 82, respectively.

If, for example, the digital fluorescence image 20 is a monochrome image, it may first be converted, in a step 126, to a color image. The digital fluorescence emulation filter 120 may then be applied, in a step 128, in the same manner as the digital background-emulation filter 110 is applied to the digital white-light color image 4.

In another variant of step 128, a pseudo-color defined by the digital fluorescence emulation filter 120 may be assigned to the digital fluorescence image 20. This may be done without conversion into a color image to save memory space and to keep processing fast.

In another step 130, the relative intensity and/or brightness of the at least one digital white-light color image 4 and the at least one digital fluorescence image 20 is adjusted to match the relative intensity and/or brightness of the background and the fluorescence in the type 82, or the digital color output image 84 produced by type 82, respectively. If the relative intensity and/or brightness is adjusted in step 130, a luminosity function, such as a CIE luminosity function, may be used. For adjusting the relative intensity and/or brightness, a digital attenuation filter 131 or a library 122 containing a plurality of digital attenuation filters 131 may be used.

Step 130 may also be integrated into at least one of steps 114 and 128 if any attenuation of the background light and/or the fluorescence light in the type 82 is already taken into account in the settings of at least one of the digital background-emulation filter 110 and the digital fluorescence emulation filter 120.

In step 132, the at least one digital white-light color image 4 and the at least one digital fluorescence image 20 are combined. For example, the at least one digital white-light color image 4 and the at least one digital fluorescence image 20 may be merged as described in EP 3 205 254 A1, which is herewith included in its entirety by reference.

The resulting digital emulated output image 72 is then displayed or further processed in a step 134.

One possible step 134 for further processing the digital emulated output image 72 is explained in the following with reference to FIGS. 4 to 6D.

As explained above, there is a need, in practice, to slowly acquaint a surgeon with the capabilities of a new technology, as implemented e.g. in the type 63 of fluorescence microscope or endoscope 1. The type 63 obtains more data due to the strict separation of visible-light data and fluorescence data compared to the type 82. Thus, step 134 may be used to display the difference between the fluorescence data obtained by the type 63 as compared to the type 82.

This is explained with reference to FIG. 4, which shows a schematic representation of an exemplary embodiment of step 134. Step 134 is preferably executed in the image-processing device 64 or, in particular, in the image processor 73.

In a first step 140, the digital emulated output image 72, which represents the digital color output image 84 that is generated by the first type 82 or, alternatively, the at least one digital fluorescence image 20, is filtered using a digital fluorescence extraction filter 142. The digital fluorescence extraction filter 142 corresponds preferably to the pass band 98 of the optical recording filter 88 as used in the type 82. The digital fluorescence extraction 142 is configured to block wavelengths λ that are outside the pass band 98. A library 112 of a plurality of different digital fluorescence extraction filters 142 may be provided, so that different variants of type 82 can be considered in step 134. The individual digital fluorescence extraction filters 142 may either be individually selected by a user or be automatically selected if the user chooses a particular variant of type 82 together with other digital filters, as described above.

The digital image 144 after the filtering step 140 contains only the fluorescence wavelengths of the fluorophore 8 that do not contain any crosstalk from the combined fluorescence excitation and background illumination light 36, 40 of type 82. Digital image 144 may be in a color format, such as RGB. Preferably, the digital image 144 and the digital fluorescence image 20 are in the same format. If this is not the case, at least one of the images 144, 20 may be converted so that they are in the same format. The step 146 of converting at least one of the images 72, 20 is shown, for exemplary purposes, only for the at least one digital fluorescence image 20. It may alternatively or cumulatively also be carried out for the digital emulated output image 72, and may, in particular, be integrated into step 140.

After the optional format conversion, the digital image 144 and the digital fluorescence image 20 are compared with one another in step 148. Preferably, the images to be compared are normalized. The comparison 148 results in a digital difference image 150.

In step 152, the difference between the fluorescence contained in the digital emulated output image 72 and the digital fluorescence image 20 is marked with a digital image pattern 154. This step may be carried out by a pattern generator 156, which may be a hardware device, a software device or a combination of both a hardware and a software device. The pattern generator 156 is part of the image-processing device 64 or the image processor 73, respectively.

At step 152, the digital difference image 150 may be merged with at least one of the digital fluorescence image 20, the digital white-light color image 4, a pseudo-color 162 and the digital image pattern 154. This results in a digital patterned output image 158, which, in a step 160, may be further processed or displayed.

In a variant of step 134, the digital fluorescence extraction filter 142 is applied—e.g. by the image processor 73—exclusively to the at least one digital fluorescence image 20. In this case, the digital fluorescence extraction filter 142 is different from the one described above and applied to the digital emulated output image 72. The digital fluorescence extraction filter 142, which is applied to the at least one digital fluorescence image 20 may be a digital histogram-matching filter which either adjusts the contrast of the digital fluorescence image 20 to match the contrast of the fluorescence recorded by the first type 82. Alternatively, application of the digital histogram-matching filter may directly result in the digital different image 150. The digital fluorescence extraction filter 142 may be determined experimentally for different variants of the image-recording system 62. Application of the digital fluorescence extraction filter 142 may directly result in the digital difference image 150, i.e. the digital fluorescence extraction filter 142 may directly extract the difference between the fluorescence as captured by the first type and by the second type of microscope or endoscope.

The pattern generator 156 preferably has access to at least one digital image pattern 154 and at least one pseudo-color 162. The digital image pattern may provide e.g. a mask which may be spatially uniform or spatially varying, and/or temporally varying. The pseudo-color 162 is assigned to the digital image pattern to make it more visible and to ensure that it stands out from the rest of the digital type-difference output image 158. In a library 112, a plurality of different digital image patterns 154 and/or of different pseudo-colors 162 may be provided, e.g. in the storage section 66. The individual digital image pattern 154 and/or pseudo-color 162 used in the pattern generation step 152 may be selected automatically by the image-processing device 64 or manually by a user.

The intensity of the pseudo-color 162 of the digital image pattern 154 is, in one example, modulated dependent upon the intensity in the digital difference image 150. Thus, the intensity, contrast and/or temporal rate of change of the digital image pattern 154 at a location, such as a pixel, depends on the intensity of the digital difference image 150 at the same location or pixel. This allows the digital image pattern displayed in the digital type-difference image 158 to be adapted to the actual absolute difference between the fluorescence captured in the digital fluorescence image 20, on the one hand, and the fluorescence captured in the digital emulated output image 72, on the other.

The digital image pattern 150 having pseudo-color 162 is, in step 152, preferably merged with one of the digital fluorescence image 20 and/or the digital white-light color image 4. The merging may take place in one single step together with assigning the digital image pattern 154 to the digital difference image 150.

In step 152, thresholds may be defined which control application of the digital image pattern 154. For example, the selected digital image pattern 154 may be only applied if the intensity in the digital difference image 150 or a difference between the fluorescence recorded in the at least one digital emulated output image and the at least one digital fluorescence image 20 exceeds a threshold which may be computed automatically from the intensity distribution in the digital difference image 150, or selected manually by a user. Alternatively or cumulatively, the digital image pattern 154 may only be applied if this difference exceeds a lower threshold, which, like the upper threshold, may also be determined either automatically or manually. Further, the digital image pattern 154 may only be applied in a region which has a predetermined minimum size, such as 5×5 or 10×10 pixels.

A preferably digital switch 164 may be provided to select which image or images of the group containing the digital emulated output image 72, the digital fluorescence image 20 and the digital white-light color image 4 may be selected as a basis for the merging of the digital image pattern 154 and the digital difference image 150 in step 152. The one or more images 4, 20, 72 serve as a background on which the digital image pattern 154 is displayed. For example, if the digital emulated output image 72 is selected by digital switch 164, the digital image pattern 154 will be displayed in an area of the digital emulated output image 72 in which no fluorescence was visible because it was either blocked by the optical recording filter 88 and/or its brightness or intensity was lower than brightness or intensity of the background illumination light. If the digital fluorescence image 20 is used at step 152, the digital image pattern 154 shows, on the digital fluorescence image 20 as background, those regions of fluorescence that are not shown in the digital emulated output image 72 or, correspondingly, have not been captured by the type 82.

In addition, the digital switch 164 may be configured to also input the at least one digital white-light color image 4 to the pattern generation and merging step 152. In this case, the white-light illuminated background will also be visible.

An example of a digital patterned output image 158 is shown in FIG. 5. The digital patterned output image 158 may contain at least one region 166, in which there is no difference in the fluorescence of the at least one fluorophore 8 between the digital emulated output image 72 and the digital fluorescence image 20 that served as the basis for the digital emulated output image 72 in question. The region 166 is preferably not marked in a digital image pattern 154, but may be assigned a pseudo-color, which preferably corresponds to the fluorescing color, i.e. the fluorescence emission spectrum, of the fluorophore 8.

The digital type-difference output image 158 may further contain a background 168, which may also not be marked with a digital image pattern 154. The background 168 comprises those regions in the digital fluorescence image 20 where there is not fluorescence of the fluorophore 8 and/or where the intensity of the fluorescence is below a threshold which again may be automatically determined from image statistics or manually determined by a user. The image displayed in the background 168 may be determined by the switch 164 as explained above.

Finally, the digital patterned output image 158 may contain at least one patterned region 170, in which fluorescence of the fluorophore 8—preferably above an automatically or user-defined intensity—has been recorded in the digital fluorescence image 20 but is not displayed in the digital emulated output image 72. The patterned region 170 thus represents the region in which the type 63 detects fluorescence, but the type 82 would not detect fluorescence. In the patterned region 170, the digital image pattern 154 is applied.

Detail V, depicted in FIGS. 6A to 6D, shows some examples of digital image patterns 154 that may be used in the digital type-difference output image 158.

In FIG. 6A, an outline 172 is used to mark the border of the patterned region 170 adjacent to the regions 166 and 168. The outline 172 may have a spatially varying pattern, e.g. by being dotted or dashed. Further, the outline 172 may be temporally varying, as indicated by arrow 174. Subsequent frames of digital type-difference output images 158 may e.g. contain the spatially varying outline 172 at different locations, so that an animated outline 172 results. The patterned region 170 itself may remain unchanged and not be filled by a digital image pattern 154. The digital image pattern 154 is restricted to the border of the patterned region 170.

As shown in FIG. 6B, the outline 172 may also be a temporally static outline.

Of course, if, in e.g. a time series 24 of digital images, the extent of the regions 166, 168, 170 changes as the underlying digital fluorescence images 20 and digital white-light color images 4 change, the outline 172 of the patterned region may shift. This, however, is not considered to constitute a temporal variation of the pattern.

In FIG. 6C, a digital image pattern 154 comprises hatching 176. The hatching 176 is temporally stationary and only spatially varying. The extent of the pattern is determined by the extent of the region 166. The digital image pattern 154 may be combined with any type of outline 172 or may not have an outline.

FIG. 6D shows a digital image pattern 154 which comprises temporally varying hatching 176, as indicated by arrow 174. For example, the digital image pattern 154 may be animated to give the impression that it is moving in the direction of arrow 174.

REFERENCE NUMERALS 1 fluorescence microscope or endoscope of a certain type
2 camera system
4 digital white-light color image
6 object
8 fluorophore
10 illumination system
12 fluorescent region or area
14 live tissue
16 absorption spectrum
18 fluorescence spectrum
20 digital fluorescence image
22 digital monochrome image
24 time series of digital images
26 pixel
28 location
30 RGB camera
32 fluorescence camera
34 background illumination source
35 fluorescence excitation source
36 background illumination light
38 reflected background illumination light
40 fluorescence excitation light
42 fluorescence light
43 fluorescence excitation spectrum
44 optical filter system
46 fluorescence excitation filter
48 observation area 50 fluorescence excitation pass band
52 fluorescence emission filter
54 fluorescence emission pass band
56 background illumination filter
58 filter characteristics of background illumination filter
60 white-light recording filter
61 filter characteristics of white-light recording filter
62 image-recording system
63 (second) type of fluorescence microscope or endoscope
64 image-processing device
66 storage section
68 input section
70 output section
72 digital emulated output image
73 image processor
74 display device
76 monitor
78 eyepiece
80 AR or VR goggles
82 different or first type of fluorescence microscope or endoscope
84 digital color output image
86 illumination filter
88 optical recording filter
90 light source
92 color camera
94 pass band of illumination filter
95 stop band of illumination filter
96 filter characteristics of recording filter
98 narrow band of filter characteristics of recording filter
100 attenuation band of recording filter
101 background illumination filter
108 type-emulation module
110 digital background-emulation filter
112 library of digital filters
114 application of digital background-emulation filter to digital white-light color image
116 sub-library of library
117 digital illumination filter
118 digital recording filter
120 digital fluorescence emulation filter
122 library of digital fluorescence emulation filters
124 sub-library of library
126 conversion to color image
128 application of digital fluorescence emulation filter to digital fluorescence image
130 adjustment of relative intensity or brightness of digital white-light color image and digital fluorescence image
131 digital attenuation filter
132 combination of digital white-light color image and digital fluorescence image
134 display or further processing of digital emulated output image
140 filtering of the digital emulated output image
142 digital fluorescence extraction filter
144 digital image
146 image camera
148 comparison of digital output image and digital fluorescence image
150 digital difference image
152 pattern generation and merging
154 digital image pattern
156 pattern generator
158 digital patterned output image
160 further processed or displayed
162 pseudo-color
164 digital switch
166 region of difference
168 background region
170 patterned region
172 outline
174 arrow
176 hatching

What is claimed is:

1. An image-processing device (64) for emulating a first type (82) of fluorescence observation device (1) on a second, different type (63) of fluorescence observation device (1),
the image-processing device (64) comprising an image processor (73) and being configured to retrieve at least one digital fluorescence image (20);
the at least one digital fluorescence image (20) representing an object (6) recorded by an image recording system (62) of the second type (63) of fluorescence observation device (1) in a fluorescence spectrum (18) of a fluorophore (8);
the image-processing device (64) comprising a type-emulation module (108), the type-emulation module being representative of an image-recording system (62) of the first type (82) of fluorescence observation device (1);
the image processor (73) being configured to apply the type-emulation module (108) to the at least one digital fluorescence image and to compute a digital emulated fluorescence output image (72) from the application of the type-emulation module (108) to the at least one digital fluorescence image;
the image-processing device (64) being further configured to output the digital emulated output image;
wherein the type-emulation module (108) comprises a digital background-emulation filter (110), the digital background-emulation filter being representative of at least one of:
a background illumination spectrum (101) of a light source (90) of the first type (82) of fluorescence observation device,
an optical illumination filter (86) located between the light source and an observation area (48) of the first type of fluorescence observation device, and
an optical recording filter (88) located between a camera system (2) of the first type of fluorescence observation device and an observation area (48) of the first type of fluorescence observation device.

2. The image-processing device (64) according to claim 1, wherein the type-emulation module (108) comprises a digital fluorescence-emulation filter (120), the digital fluorescence-emulation filter (12) being representative of at least one of:
the fluorescence spectrum (18) of a fluorophore (8), and
an optical recording filter (88) located between the camera system (2) of the first type (82) of fluorescence microscope or endoscope and the observation area (48) of the first type.

3. The image-processing device (64) according to claim 1, wherein the image-processing device (64) is further configured to retrieve at least one digital white-light color image (4) recorded by the second type (63) of fluorescence observation device (1) and representing the object (6) illuminated by white light and to compute the digital emulated output image (72) from a combination of the at least one digital fluorescence image (20) to which the type-emulation module (108) has been applied and the at least one digital white-light color image.

4. The image-processing device (64) according to claim 3, wherein the image processor (73) is configured to apply the type-emulating module (108) to the at least one digital white-light color image (4) and to compute the digital emulated output image (72) from a combination of the at least one digital fluorescence image (20) to which the type-emulation module (108) has been applied and the at least one digital white-light color image to which the type-emulation module (108) has been applied.

5. The image-processing device (64) according to claim 3, wherein the type-emulation module (108) comprises a digital attenuation filter (131), and wherein the image processor (73) is configured to adjust an intensity (I) of the at least one digital white-light color image (4) and the at least one digital fluorescence image (20) relative to one another by applying the digital attenuation filter to at least one of the at least one digital white-light color image and the at least one digital fluorescence image.

6. An image-processing device (64) for emulating a first type (82) of fluorescence observation device (1) on a second, different type (63) of fluorescence observation device (1),
the image-processing device (64) comprising an image processor (73) and being configured to retrieve at least one digital fluorescence image (20);
the at least one digital fluorescence image (20) representing an object (6) recorded by an image recording system (62) of the second type (63) of fluorescence observation device (1) in a fluorescence spectrum (18) of a fluorophore (8);
the image-processing device (64) comprising a type-emulation module (108), the type-emulation module being representative of an image-recording system (62) of the first type (82) of fluorescence observation device (1);
the image processor (73) being configured to apply the type-emulation module (108) to the at least one digital fluorescence image and to compute a digital emulated fluorescence output image (72) from the application of the type-emulation module (108) to the at least one digital fluorescence image;
the image-processing device (64) being further configured to output the digital emulated output image;
wherein the image processor (73) comprises a pattern generator (156) configured to generate a digital image pattern (154),
wherein the image processor (73) is configured to compute a difference between the at least one digital emulated output image computed using the type-emulation module (108) and at least one digital emulated output image computed without using the type-emulation module or computed using another type-emulation module (108), and
wherein the image processor is further configured to compute at least one digital patterned image (150) from a combination of the at least one digital emulated output image and the digital image pattern, the digital image pattern being assigned to the difference.

7. A fluorescence observation device (1) comprising:
an image-recording system (62), the image-recording system being configured to record at least one digital fluorescence image (20) in the fluorescence spectrum (18) of a fluorophore (8);
an image-processing device (64) comprising an image processor (73) and configured to receive the at least one digital fluorescence image (29) from the image-recording system;

the image-processing device (64) comprising a type-emulation module (108), the type-emulation module being representative of a different image-recording system (62) of a different type (82) of fluorescence observation device (1), wherein the type-emulation module (108) comprises a digital background-emulation filter (110), the digital background-emulation filter being representative of at least one of: (i) a background illumination spectrum (101) of a light source (90) of the different type (82) of fluorescence observation device, (ii) an optical illumination filter (86) located between the light source and an observation area (48) of the different type of fluorescence observation device, and (iii) an optical recording filter (88) located between a camera system (2) of the different type of fluorescence observation device and an observation area (48) of the different type of fluorescence observation device;
the image processor (73) being configured to apply the type-emulation module (108) to the at least one digital fluorescence image and to compute at least one digital emulated fluorescence output image (72) from the application of the type-emulation module (108) to the at least one digital fluorescence image; and
at least one display device (74), the at least one display device being configured to display the at least one digital emulated fluorescence output image (72).

8. A method for emulating a first type (82) of fluorescence observation device (1) on a second type (63) of fluorescence display device (1), the method comprising the following steps:
retrieving at least one digital fluorescence image (20) representing an object (6) in a fluorescence spectrum (18) of a fluorophore (8) and recorded by the second type of fluorescence observation device (1) using an image-recording system (62);
computing a digital emulated output image (72) from the at least one digital fluorescence image; and
outputting the digital emulated output image for at least one of displaying or further processing;
wherein the step of computing the at least one digital emulated output image comprises the step of:
applying a type-emulation module (108) to the at least one digital fluorescence image, the type-emulation module being representative of the image-recording system (62) of the first type (82) of a fluorescence observation device (1);
wherein the step of applying the type-emulation module (108) further comprises merging a pseudo-color with the at least one digital fluorescence image (20) depending on a digital fluorescence-emulation filter (120) of the type-emulation module.

9. The method according to claim 8, further comprising the following step:
acquiring at least one digital white-light color image (4) representing the object (6) recorded in white light, and
wherein the step of computing the at least one digital emulated output image comprises at least one of the following steps:
applying the type-emulation module (108) to the at least one digital white-light color image (4), and
generating the at least one digital emulated output image from the at least one digital fluorescence image, to which the type-emulation module (108) was applied, and the at least one digital white-light color image.

10. The method according to claim 9, wherein applying the type-emulation module (108) further comprises applying a digital background-emulation filter (110) to the at least one digital white-light color image (4) for altering the spectrum of the at least one digital white-light color image (4).

11. The method according to claim 8, wherein the second type (63) of fluorescence display device is switched between emulating different types of fluorescence display devices using different type-emulation modules (108).

12. A non-transitory computer-readable medium storing a computer program comprising instructions which, when the program is executed by a computer, cause the computer to carry out the method according to claim 8.

13. A method for emulating a first type (82) of fluorescence observation device (1) on a second type (63) of fluorescence display device (1), the method comprising the following steps:
 retrieving at least one digital fluorescence image (20) representing an object (6) in a fluorescence spectrum (18) of a fluorophore (8) and recorded by the second type of fluorescence observation device (1) using an image-recording system (62);
 computing a digital emulated output image (72) from the at least one digital fluorescence image; and
 outputting the digital emulated output image for at least one of displaying or further processing;
 wherein the step of computing the at least one digital emulated output image comprises the step of:
 applying a type-emulation module (108) to the at least one digital fluorescence image, the type-emulation module being representative of the image-recording system (62) of the first type (82) of a fluorescence observation device (1);
 wherein the method further comprises acquiring at least one digital white-light color image (4) representing the object (6) recorded in white light, and
 wherein the step of computing the at least one digital emulated output image comprises at least one of the following steps:
 applying the type-emulation module (108) to the at least one digital white-light color image (4), and
 generating the at least one digital emulated output image from the at least one digital fluorescence image, to which the type-emulation module (108) was applied, and the at least one digital white-light color image;
 wherein a difference between the at least one digital emulated output image (72) obtained by using a type-emulation module (108), and at least one digital emulated output image obtained from the at least one digital white-light color image (4) and the at least one digital fluorescence image (20) without using a type-emulation module, is determined and marked with a digital image pattern (154) in the at least one digital emulated output image.

\* \* \* \* \*